United States Patent [19]
Cook et al.

[11] Patent Number: 6,166,197
[45] Date of Patent: Dec. 26, 2000

[54] OLIGOMERIC COMPOUNDS HAVING PYRIMIDINE NUCLEOTIDE (S) WITH 2'AND 5 SUBSTITUTIONS

[75] Inventors: Phillip Dan Cook; Yogesh S. Sanghvi, both of San Marcos; Kelly G. Sprankle, Vista; Bruce S. Ross, Carlsbad; Rich H. Griffey, Vista, all of Calif.

[73] Assignee: ISIS Pharmaceuticals, Inc., Carlsbad, Calif.

[21] Appl. No.: 08/398,901

[22] Filed: Mar. 6, 1995

[51] Int. Cl.$^7$ .......................... C07H 19/00; C07H 21/00; C07H 21/02; C07H 21/04
[52] U.S. Cl. ............................ 536/24.5; 435/6; 536/22.1; 536/23.1; 536/24.3; 536/25.3
[58] Field of Search ................................. 435/6; 536/22.1, 536/23.1, 24.3, 25.3, 24.5

[56] References Cited

U.S. PATENT DOCUMENTS

| | | | |
|---|---|---|---|
| 3,687,808 | 8/1972 | Merigan et al. | 195/28 N |
| 4,511,713 | 4/1985 | Miller et al. | 536/27 |
| 5,013,830 | 5/1991 | Ohtsuka et al. | 536/27 |
| 5,210,264 | 5/1993 | Yau | 558/167 |
| 5,386,023 | 1/1995 | Sanghvi et al. | 536/25.3 |
| 5,466,786 | 11/1995 | Buhr et al. | 536/26.26 |
| 5,470,967 | 11/1995 | Huie et al. | 536/24.3 |
| 5,606,049 | 2/1997 | Vaghefi | 536/28.5 |
| 5,750,673 | 5/1998 | Martin | 536/26.1 |

FOREIGN PATENT DOCUMENTS

| | | |
|---|---|---|
| 0260032 A3 | 3/1988 | European Pat. Off. . |
| 0339842 A2 | 11/1989 | European Pat. Off. . |
| 0614907 | 9/1994 | European Pat. Off. ........ C07H 21/00 |
| 0 629 633 A2 | 12/1994 | European Pat. Off. . |
| 0 714 907 A1 | 6/1996 | European Pat. Off. . |
| 4110085 A1 | 10/1992 | Germany . |
| 2-264792 | 10/1990 | Japan . |
| 6-507883 | 9/1994 | Japan . |
| 6-345791 | 12/1994 | Japan . |
| 7-2889 | 1/1995 | Japan . |
| 7-300493 | 11/1995 | Japan . |
| 8-208686 | 8/1996 | Japan . |
| 9-508134 | 8/1997 | Japan . |
| WO 91/15499 | 10/1991 | WIPO . |
| WO 92/05186 | 4/1992 | WIPO . |
| WO 92/13869 | 8/1992 | WIPO . |
| WO 93/10820 | 6/1993 | WIPO . |
| WO 94/02499 | 2/1994 | WIPO . |
| WO 94/17094 | 8/1994 | WIPO . |
| WO 95/20597 | 8/1995 | WIPO . |
| WO 95/35102 | 12/1995 | WIPO . |

OTHER PUBLICATIONS

Edmonds et al. "Structural Characterization of four ribose–methylated nucleosides from teh transfer RNA of extremely thermophilic archaebacteria" J. Chem. Soc. Chem. Comm. pp. 909–910, 1987.

Shimizu et al. "Effects of 5–methyl substitution in 2'O–methyloligo(pyrimidine)nucleotides on triple–helix formation" Bioorganic & Medicinal Chemistry Letters vol. 4, No. 8, pp. 1029–1032, 1994.

Gotfredsen et al. "Novel Oligonucleotide analogues containing a 2'–O–Methylarabinonucleoside" Tetrahedron Letters vol. 35, No. 37, pp. 6941–6944, 1994.

Morvan, et al., "Comparative Evaluation of Seven Oligonucleotide Analogues as Potential Antisense Agents," Jour.Med. Chem., 1993, vol. 36, pp. 280–287.

Monia et al., "Evaluation of 2'–Modified Oligonucleotides Containing 2'–Deoxy Gaps as Antisense Inhibitors of Gene Expression,"Jour. Bio. Chem., Jul. 5, 1993, vol. 268, No. 19, pp. 14514–14522.

Kawasaki, et al., "Uniformly Modified 2'–Deoxy–2'–Fluoro Phosphorothioate Oligonucleotides as Nuclease–Resistant Antisense Compounds w/High Affinity & Specificity for RNA Targets", Jour. Med. Chem., 1993, vol. 36, pp. 831–841.

Wagner et al., "Antisense Gene Inhibition by Oligonucleotides Containing C–5 Propyne Pyrimidines," Science, Jun. 4, 1993, vol. 260, pp. 1510–1513.

Lamond, et al., Antisense Oligonucleotides Made of 2'–O–alkyl RNA: Their Properties & Applications in RNA Biochemistry. FEBS Letters, Jun. 1993, vol. 325, Number, 1,2, pp. 123–127.

Alul, R. et al., "Oxalyl–CPG: a Labile Support for Synthesis of Sensitive Oligonucleotide Derivatives", Nucleic Acids Research 1991, 19(7), 1527–1532.

Beaucage, S. and Iyer, "Advances in the Synthesis of Oligonucleotides by the Phosphoramidite Approach", Tetrahedron 1992, 48(12), 2223–2311.

Bielinska, A. et al., "Regulation of Gene Expression with Double–Stranded Phosphorothioate Oligonucleotides", Science 1990, 250, 997–1000.

Blackburn, G. and Gait, "Nucleic Acids in Chemistry and Biology", Chapter 3, p. 98, IRL PRess, New York, 1990.

Bradford, M., "A Rapid and Sensitive Method for the Quantitation of Microgram Quantities of Protein Utilizing the Principle of Protein–Dye Binding", Analytical Biochemistry 1976, 72, 248–254.

Coussens, L. et al., "Multiple, Distinct Forms of Bovine and Human Protein Kinase C Suggest Diversity in Cellular Signaling Pathways", Science 1986, 233, 859–866.

(List continued on next page.)

Primary Examiner—Jezia Riley
Attorney, Agent, or Firm—Woodstock Washburn Kurtz Mackiewicz & Norris LLP

[57] ABSTRACT

Oligonucleotide analogs are disclosed having pyrimidine monomeric sub-units therein that are modified at the 2' and 5 positions. Monomeric sub-units having these modifications may be further modified at the 2 position.

3 Claims, No Drawings

OTHER PUBLICATIONS

Dean, N. et al., "Inhibition of Protein Kinase C–α Expression in Human A549 Cells by Antisense Oligonucleotides Inhibits Induction of Intercellular Adhesion Molcelule 1 (ICAM–1) mRNA by Phorbol Esters", *The J. of Biol. Chem.* 1994, 269(23), 16416–16424.

Englisch, U. and Gauss, "Chemically Modified Oligonucleotides as Probes and Inhibitors", *Angew. Chem. Int. Ed. Engl.* 1991, 30, 613–629.

Gibson, K. and Benkovic, "Synthesis and Application of Derivatizable Oligonucleotides", *Nucleic Acids Research* 1987, 15(16), 6455–6467.

Graham, F.G. and Van der Eb, "A New Technique for the Assay of Infectivity of Human Adenovirus 5 DNA", *Virology* 1973, 52, 456–467.

Greene, T. and Wuts, "Protective Groups in Organic Synthesis", John Wiley & Sons, New York, 2nd edition, 1991, Chap. 2, 6, 7.

Haralambidis, J. et al., "Preparation of Base–Modified Nucleosides Suitable for Non–Radioactive Label Attachment and Their Incorporation Into Synthetic Oligodeoxyribonucleotides", *Nucleic Acids Research* 1987, 15(12), 4857–4875.

Kroschwitz, J., ed., "Concise Encyclopedia of Polymer Science and Engineering", pp. 858–859, John Wiley & Sons, New York, 1990.

Manoharan, M., "Designer Antisense Oligonucleotides: Conjugation Chemistry and Functionality Placement", pp. 310–312 in "Antisense Research and Applications", Crooke and Lebleu, eds., CRC Press, Boca Raton, 1993.

Miesfeld, R. et al., "Genetic Complementation of a Glucocoricoid Receptor Deficiency by Expression of Cloned Receptor cDNA", *Cell* 1986, 46, 389–399.

Vorbruggen, H. et al., "A Simple New Synthesis of 2–Thiopyrimidine Nucleosides", *Angew. Chem. Internat. Edit.* 1969, 12, 976–977.

Vorbruggen, H. and Strehlke, "Eine einfache Synthese von 2–Thiopyrimidin–nucleosiden", *Chem. Ber.* 1973, 106, 3039–3061.

Wright, P. et al., "Large Scale Synthesis of Oligonucleotides via Phosphoramidite Nucleosides and a High–loaded Polystyrene Support", *Tetrahedron Letters* 1993, 34(21), 3373–3376.

Wu, H. et al., "Inhibition of In Vitro Transcription by Specific Double–Stranded Oligodeoxyribonucleotides", *Gene* 1990, 89, 203–209.

Sambrook, J. et al., "Molecular Cloning, A Laboratory Manual", Cold Spring Harbor Laboratory Press, 1989.

Ausubel, F.M. et al., eds., "Current Protocols in Molecular Biology", John Wiley & Sons, New York, 1993.

Sterzycki, R. et al, "Synthesis and Anti–HIV Activity of Several 2'–Fluoro–Containing Pyrimidine Nucleosides", *J. Med. Chem.*, 1990, 33, pp. 2150–2157.

Fraser, A. et al., "Synthesis & Conformational Properties of 2'–Deoxy–2'–methylthio–pyrimidine & –purine Nucleosides:Potential Antisense Applications", *Jour. of Heterocyclic Chem.*, 1993, 30, pp. 1277–1287.

Uhlman, E. et al., "Antisense Oligonucleotides: A New Therapeutic Principle", *Chem. Reviews*, 1990, vol.90–No.4, pp. 543–584.

Solomons, T.W., "Organic Chemistry", John Wiley and Sons, New York, Fifth Edition, 1992, p. 433.

March, J., "Advanced Organic Chemistry–Reactions, Mechanisms, and Structure", John Wiley and Sons, New York, Third Edition, A Wiley–Interscience Publication, 1985, pp. 227–229.

Arya et al., "Inhibition of Synthesis of Murine Leukemia Virus in Cultured Cells by Polyribonucleotides and Their 2'–O–Alkyl Derivatives", *Molecular Pharm.*, 1975, 12, 234–241.

Chavis et al., "Synthesis of 2',3'–Differentiated Ribonucleotides via Glycosylation Reactions with 2–O–Me or 2–O–TBDMS Ribofuranose Derivatives. 1. Pyrimidine Series", *J. Org. Chem.*, 1982, 47, 202–206.

Cotten et al., "2'–O–methyl, 2'–O–ethyl oligoribonucleotides and phosphorothioate oligodeoxyribonucleotides as inhibitors of the in vitro U7 snRNP–dependent mRNA processing event", *Nucl. Acids Res.*, 1991, 19(10), 2629–2635.

Divakar et al., "Reaction Between 2,2'–Anhydro–1–β–D–arabinofuranosyluracil and Thiolate Ions", *J. Chem. Soc. Perkin Trans.*, 1982, 1625–1628.

Edmonds et al., "Structural Characterization of Four Ribose–methylated Nucleosides from the Transfer RNA of Extremely Thermophilic Archaebacteria", *J. Chem. Soc., Chem. Commun.*, 1987, 909–910.

Guinosso et al., "Synthesis and Biophysical and Biological Evaluation of 2'–Modified Antisense Oligonucleotides", *Nucleotides & Nucleotides*, 1991, 10(1–3), 259–262.

Inoue et al., "Synthesis and properties of novel nucleic acid probes", *Nucl. Acids Res.*, 1985, 165–168.

Inoue et al., "Synthesis and hybridization studies on two complementary nona(2'–O–methyl)ribonucleotides", *Nucl. Acids Res.*, 1987, 15(15), 6131–6148.

Iribarren et al., "2'–O–Alkyl oligoribonucleotides as antisense probes", *Proc. Natl. Acad. Sci. USA*, 1990, 87, 7747–7751.

Johansson et al., "Target–specific arrest of mRNA translation by antisense 2'–O–alkyloligoribonucleotides", *Nucl. Acids Res.*, 1994, 22(22), 4591–4598.

Keller et al., "A General Method for the Synthesis of 2'–O–Modified Ribonucleosides", *Helv. Chim. Acta*, 1993, 76, 884–892.

Kielanowska et al., "Preparation and properties of poly 2'–O–ethylcytidylic acid", *Nucl. Acids Res.*, 1976, 3(3), 817–824.

Kusmierek et al., "Alkylation of Cytidine–5'–Phosphate: Mechanisms of Alkylation, Influence of O'–Alkylation of Susceptibility of Pyrimidine Nucleotides to Some Nucleolytic Enzymes, and Synthesis of 2'–O–Alkyl Polynucleotides", *Acta Biochimica Polonica*, 1973, 20(4), 365–381.

Kusmierek et al., "Preparation and stability of the helical form of poly 2'–O–ethyluridylic acid", *Biochem. Biophy. Res. Commun.*, 1973, 53(2), 406–412.

Kusmierek et al., "Preparation of O'–Alkyl Derivatives of Cytosine and Uracil Nucleosides", *Biochem.*, 1973, 12(2), 194–200.

Martin, "A New Access to 2'–O–Alkylated Ribonucleosides and Properties of 2'–O–Alkylated Oligoribonucleotides", *Helv. Chim. Acta*, 1995, 78, 486–504.

Mikke et al., "Oligo(dG)$_{12-18}$ aggregates result in non–homogeneity of oligo(dG)$_{12-18}$ poly© type primer template", *Nucl. Acids Res.*, 1977, 4(4), 1111–1112.

Mikke et al., "Poly 2'–O–ethylcytidylate, an inhibitor and poor template for AMV reverse transcriptase", *Nuc. Acids Res.*, 1976, 3(6), 1603–1611.

Ransford et al., "2'-O-Ethyl Pyrimidine Nucleosides (1)", *J. Carbohydrates, Nucleosides, Nucleotides*, 1974, 1(3), 275–278.

Robins et al., "Nucleic Acid Related Compounds. 1. Methylation and Transformation of 4-Methoxy-2-pyrimidinone 1-β-D-Ribofuranoside into 2'-O-Methyl Nucleoside Components of Ribonucleic Acid, Their Analogs, and Derivatives", *Biochem.*, 1971, 10(19), 3591–3597.

Rottman et al., "Influence of 2'-O-Alkylation on the Structure of Single-Stranded Polynucleotides and the Stabiltiy of 2'-O-Alkylated Polynucleotide Complexes", *Biochem.*, 1974, 13(13), 2762–2771.

Singer et al., "$O^2$-Alkycytidine—A New Major Product of Neutral, Aqueous Reaction of Cytidine with Carcinogens", *FEBS Lett.*, 1976, 63(1), 85–88.

Singer et al., "Alkylation of Ribose in RNA Reacted with Ethylnitrosourea at Neutrality", *Biochem.*, 1976, 15(23), 5052–5057.

Sproat et al., "2'-O-Alkylologoribonucleotides: Synthesis and Applications in Studying RNA Splicing", *Nucleosides & Nucleotides*, 1991, 10(1–3), 25–36.

Tazawa et al., "A Novel Procedure for the Synthesis of 2'-O-Alkyl Nucleotides", *Biochem.*, 1972, 11(26), 4931–4937.

Verheyden et al., "Synthesis of Some Pyrimidine 2'-Amino-2'-deoxynucleosides", *J. Org. Chem.*, 1971, 36(2), 250–254.

Wagner et al., "Preparation and Synthetic Utility of Some Organotin Derivatives of Nucleosides", *J. Org. Chem.*, 1974, 39(1), 24–30.

Wagner et al., "A simple procedure for the preparation of protected 2'-O-methyl or 2'-O-ethyl ribonucleosides-3'-O-phosphoramidites", *Nucl. Acids Res.*, 1991, 19(24), 5965–5971.

Kois, P. et al., "Synthesis and Some Properties of Modified Oligonucleotides. 2. Oligonucleotides Containing 2'-Deoxy-2'-Fluoro-β-D-Arabinofuranosyl Pyrimidine Nucleosides," *Nucleosides & Nucleotides*, 1993, 12(10), 1093–1109.

Krug, A. et al., "Synthesis of oligonucleotide probes containing 2'-deoxy-2'-fluoronucleosides for cleavage of RNA by Rnase H," *Biomed. Biochim. Acta*, 1990, 49, 161–166.

Ohtsuka, E. et al., "Studies on Transfer Ribonucleic Acids and Related Compounds. XLI. Synthesis of tRNA Fragments containing Modified Nucleosides," *Chem. Pharm. Bull.*, 1983, 31(2), 512–520.

Williams, D.M. et al., "Properties of 2'-Fluorothymidine-Containing Oligonucleotides: Interaction with Restriction Endonuclease EcoRV," *Biochem.*, 1991, 30, 4001–4009.

OLIGOMERIC COMPOUNDS HAVING PYRIMIDINE NUCLEOTIDE (S) WITH 2' AND 5 SUBSTITUTIONS

FIELD OF THE INVENTION

This invention is directed to oligomeric compounds having at least one modified pyrimidine monomeric sub-unit with modifications at both the 2' position of the sugar and the 5 position of the pyrimidine. Oligomeric compounds of the invention exhibit increased binding affinity to nucleic acids and increased nuclease resistance.

BACKGROUND OF THE INVENTION

Oligonucleotides and their analogs have been developed and used in molecular biology in certain procedures as probes, primers, linkers, adapters, and gene fragments. Modifications to oligonucleotides used in these procedures include labeling with nonisotopic labels, e.g. fluorescein, biotin, digoxigenin, alkaline phosphatase, or other reporter molecules. Other modifications have been made to the ribose phosphate backbone to increase the nuclease stability of the resulting analog. These modifications include use of methyl phosphonates, phosphorothioates, phosphorodithioate linkages, and 2'-O-methyl ribose sugar units. Further modifications, include modifications made to modulate uptake and cellular distribution. With the success of these oligonucleotides for both diagnostic and therapeutic uses, there exists an ongoing demand for improved oligonucleotide analogs.

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is a general object of such therapeutic approaches to interfere with or otherwise modulate gene expression which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as antisense agents in human clinical trials for various disease states including use as antiviral agents.

Transcription factors interact with double-stranded DNA during regulation of transcription. Oligonucleotides can serve as competitive inhibitors of transcription factors to modulate the action of transcription factors. Several recent reports describe such interactions (see Bielinska, A., et. al., *Science*, 1990, 250, 997–1000; and Wu, H., et. al., *Gene*, 1990, 89, 203–209).

In addition to such use as both indirect and direct regulators of proteins, oligonucleotides have also found use in diagnostic tests. Such diagnostic tests can be performed using biological fluids, tissues, intact cells or isolated cellular components. As with gene expression inhibition, diagnostic applications utilize the ability of oligonucleotides to hybridize with a complementary strand of nucleic acid. Hybridization is the sequence specific hydrogen bonding of oligonucleotides via Watson-Crick and/or Hoogsteen base pairs to RNA or DNA. The bases of such base pairs are said to be complementary to one another.

Oligonucleotides are also widely used as research reagents. They are useful for understanding the function of many other biological molecules as well as in the preparation of other biological molecules. For example, the use of oligonucleotides as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides, both natural and synthetic, are employed as primers in PCR technology.

Oligonucleotides are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include Synthetic oligonucleotide Probes, Screening Expression Libraries with Antibodies and Oligonucleotides, DNA Sequencing, In Vitro Amplification of DNA by the Polymerase Chain Reaction and Site-directed Mutagenesis of Cloned DNA (see Book 2 of *Molecular Cloning, A Laboratory Manual*, ibid.) and DNA-Protein Interactions and The Polymerase Chain Reaction (see Vol. 2 of *Current Protocols In Molecular Biology*, ibid).

Oligonucleotides can be synthesized to have custom properties that are tailored for a desired use. Thus a number of chemical modifications have been introduced into oligonucleotides to increase their usefulness in diagnostics, as research reagents and as therapeutic entities. Such modifications include those designed to increase binding to a target strand (i.e. increase their melting temperatures, Tm); to assist in identification of the oligonucleotide or an oligonucleotide-target complex; to increase cell penetration; to stabilize against nucleases and other enzymes that degrade or interfere with the structure or activity of the oligonucleotides; to provide a mode of disruption (terminating event) once sequence-specifically bound to a target; and to improve the pharmacokinetic properties of the oligonucleotide.

Gibson, K. J., and Benkovic, S. J., *Nucleic Acids Research*, 1987, 15, 6455–6467, discloses a phthalimide-protected 5-(3-aminopropyl)-2'-deoxyuridine nucleoside probe, which is incorporated into oligonucleotides.

Haralambidis, J., et.al., *Nucleic Acids Research*, 1987, 15, 4857–4876, discloses C-5 substituted deoxyuridines which are incorporated into oligonucleotides. The substituent has a masked primary aliphatic amino group which can be further substituted with various groups.

PCT Application WO 94/17094, filed Jan. 22 1993, published Aug. 4, 1994, discloses 5-substituted pyrimidine bases either cytosine or uracil wherein the 5-substituent is $C_{3-14}$ n-alkyl, $C_{2-8}$ (E)-n-1-alkenyl, ethynyl, or a $C_{4-12}$ n-1-alkyl group. Oligonucleotides are synthesized having one or more of these modified 5-substituted pyrimidine bases.

PCT Application No. WO 93/10820, filed Nov. 24, 1992, published Jun. 10, 1993, discloses 5-(1-propynyl)uracil and 5-(1-propynyl)cytosine or related analogs. Oligonucleotides are synthesized having one or more of these modified 5-substituted pyrimidine bases.

PCT Application No. WO 93/10820, filed Nov. 24, 1992, discloses 2' and 5 substituted pyrimidine nucleotides which are incorporated into oligonucleotides. All 2' and 5 substituted pyrimidine nucleotides of the invention have a pi bond connecting the carbon atom attached to the 5' position of the base.

SUMMARY OF THE INVENTION

The present invention provides oligomeric compounds having improved affinity for nucleic acid and having at least one monomeric sub-unit of structure I:

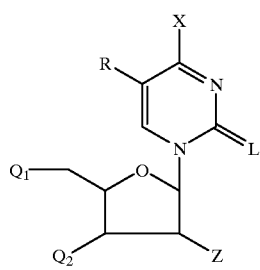

Structure I wherein:
X is hydroxyl or amino;
R is halo or $C_1$–$C_6$ alkyl or substituted $C_1$–$C_6$ alkyl wherein said substitution is halo, amino, hydroxyl, thiol, ether or thioether;
L is oxygen or sulfur;
Z is fluoro or O—$R_1X_1$, where $R_1$ is $C_1$–$C_6$ alkyl, $C_6$–$C_{10}$ aryl, $C_7$–$C_{18}$ alkaryl and $X_1$ is H, $NH_2$ or imidazole; and
One of $Q_1$ and $Q_2$ is attached via a covalent bond to a nucleotide, oligonucleotide, nucleoside, or oligonucleoside and the other of said $Q_1$ and $Q_2$, is a hydroxyl, a protected hydroxyl, an activated solid support, a nucleotide, an oligonucleotide, a nucleoside, an oligonucleoside, an oligonucleotide/nucleoside, an activated phosphate, a phosphate, an activated phosphite, or a phosphite.

In one preferred embodiment of the invention, L is oxygen. In another embodiment Z is F.

In a further embodiment of the present invention oligomeric compounds are from about 5 to 200 sub-units in length. In a more preferred embodiment oligomeric compounds are from about 5 to 50 sub-units in length. In an even more preferred embodiment the oligomeric compounds are from about 10 to 20 sub-units in length.

In another embodiment, covalent bonds between monomeric sub-units of the invention and a nucleotide, oligonucleotide, nucleoside, or oligonucleoside in the oligomeric compound are chosen from phosphodiester, phosphotriester, hydrogen phosphonate, alkylphosphonate, alkylphosphonothioate, arylphosphonothioate, phosphorothioate, phosphorodithioate, or phosphoramidate.

In a further embodiment of the present invention oligomeric compounds are prepared having a plurality of monomeric sub-units of structure I. In a preferred embodiment, oligomeric compounds having a plurality of monomeric sub-units of structure I, are prepared having the monomeric sub-units located at preselected positions. Included in a particular embodiment of the invention is oligomeric compounds having at least one monomeric sub-unit of structure II:

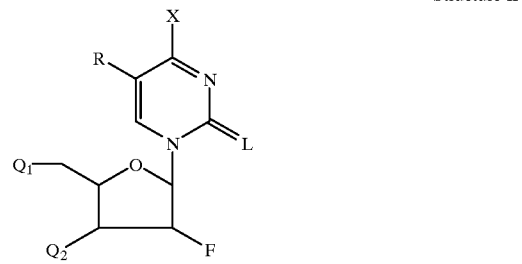

Structure II wherein:
X is hydroxyl or amino;
R is halo or $C_1$–$C_6$ alkyl or substituted $C_1$–$C_6$ alkyl wherein said substitution is halo, amino, hydroxyl, thiol, ether or thioether;
L is oxygen or sulfur; and
one of $Q_1$ and $Q_2$ is attached via a linking moiety to a nucleotide, oligonucleotide, nucleoside, or oligonucleoside and the other of said $Q_1$ and $Q_2$ is a hydroxyl, a protected hydroxyl, an activated solid support, a nucleotide, an oligonucleotide, a nucleoside, an oligonucleoside, an oligonucleotide/nucleoside, an activated phosphate, a phosphate, an activated phosphite, or a phosphite.

In a preferred embodiment of the invention L is O.

In a further embodiment, oligomeric compounds of the present invention are from about 5 to 50 sub-units in length.

In another embodiment, covalent bonds between monomeric sub-units of the invention and a nucleotide, oligonucleotide, nucleoside, or oligonucleoside in the oligomeric compound are chosen from phosphodiester, phosphotriester, hydrogen phosphonate, alkylphosphonate, alkylphosphonothioate, arylphosphonothioate, phosphorothioate, phosphorodithioate, or phosphoramidate.

In a further embodiment of the present invention oligomeric compounds are prepared having a plurality of monomeric sub-units of structure I. In a preferred embodiment, oligomeric compounds having a plurality of monomeric sub-units of structure I, are prepared having the monomeric sub-units located at preselected positions. Included in a particular embodiment of the invention is oligomeric compounds having at least one monomeric sub-unit of structure III:

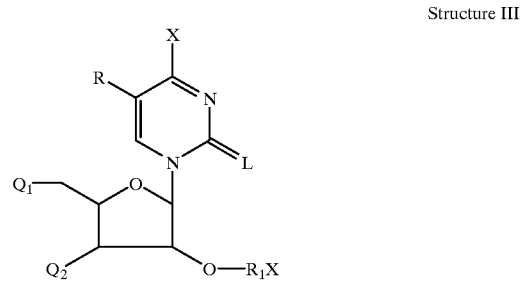

Structure III wherein:
X is hydroxyl or amino;

R is halo or $C_1$–$C_6$ alkyl or substituted $C_1$–$C_6$ alkyl wherein said substitution is halo, amino, hydroxyl, thiol, ether or thioether;

L is oxygen or sulfur;

$R_1$ is $C_1$–$C_6$ alkyl, $C_6$–$C_{10}$ aryl, $C_7$–$C_{18}$ alkaryl and $X_1$ is H, $NH_2$ or imidazole; and one of $Q_1$ and $Q_2$ is attached via a linking moiety to a nucleotide, oligonucleotide, nucleoside, or oligonucleoside and the other of said $Q_1$ and $Q_2$, is a hydroxyl, a protected hydroxyl, an activated solid support, a nucleotide, an oligonucleotide, a nucleoside, an oligonucleoside, an oligonucleotide/nucleoside, an activated phosphate, a phosphate, an activated phosphite, or a phosphite.

In a preferred embodiment of the invention, L is O.

In a further embodiment, oligomeric compounds of the present invention are from about 5 to 50 sub-units in length.

In another embodiment, covalent bonds between monomeric sub-units of the invention and a nucleotide, oligonucleotide, nucleoside, or oligonucleoside in the oligomeric compound are chosen from phosphodiester, phosphotriester, hydrogen phosphonate, alkylphosphonate, alkylphosphonothioate, arylphosphonothioate, phosphorothioate, phosphorodithioate, or phosphoramidate.

In a further embodiment of the present invention oligomeric compounds are prepared having a plurality of monomeric sub-units of structure I. In a preferred embodiment, oligomeric compounds having a plurality of monomeric sub-units of structure I, are prepared having the monomeric sub-units located at preselected positions.

DESCRIPTION OF PREFERRED EMBODIMENTS

Preferred oligomeric compounds of the invention have at least one monomeric sub-unit of Structure I. Structure I is a β-D-erythro-pentofuranosyl sugar substituted at the 2' position and coupled 1' to 1 to a 5-substituted pyrimidine through a glycosyl linkage. The 5' and 3' ends of the monomeric sub-unit can be coupled to a nucleotide, nucleoside, oligonucleotide, oligonucleoside, or a mixed oligonucleotide/nucleoside or can be a 3' or a 5' terminal end of the oligomeric compound.

Monomeric sub-units used to prepare compounds of the invention include nucleotides and nucleosides. Nucleotides include a phosphorous linking moiety whereas nucleosides have a non phosphorous linking moiety and each have a ribofuranose moiety attached through a glycosyl bond to a nucleobase.

In one aspect of the present invention the oligomeric compounds of the invention have a plurality of monomeric sub-units of Structure I. In a further aspect of the present invention the oligomeric compounds of the invention having a plurality of monomeric sub-units of Structure I, have a predetermined sequence. Monomeric sub-units of the invention can be located in predetermined positions in an oligomeric compound of predetermined sequence to increase the activity of the oligomeric compound.

Nucleobases according to the invention include purines and pyrimidines such as adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia of Polymer Science And Engineering*, pages 858–859, Kroschwitz, J. I., ed. John Wiley & Sons, 1990, and those disclosed by Englisch, et al., *Angewandte Chemie, International Edition* 1991, 30, 613.

In one aspect of the invention nucleoside dimers are incorporated into compounds of the invention. One procedure for incorporating a mixed oligo-nucleotide/nucleoside into a compound of the invention is to incorporate nucleotides, nucleoside dimers, and monomeric sub-units of Structure I into oligomeric compounds in a predetermined order using standard oligonucleotide synthesis protocols. In one aspect of the invention nucleosides, oligonucleoside, and nucleoside dimers are prepared as per the disclosures of U.S. patent application Ser. No. 08/174,379, filed Dec. 28, 1993, entitled "Hydrazine-Based & Hydroxylamine-Based Oligonucleoside Linkages & Bidirectional Synthetic Processes Therefor", also identified by attorney docket ISIS-0716; U.S. patent application Ser. No. 08/040,933, filed Mar. 31, 1993, entitled "Backbone Modified Oligonucleotide Analogs And Preparation Thereof Radical Coupling", also identified by attorney docket ISIS-0717; and U.S. patent application Ser. No. 08/040,903, filed Mar. 31, 1993, entitled "Backbone Modified Oligonucleotide Analogs And Preparation Thereof Through Reductive Coupling", also identified by attorney docket ISIS-0718, commonly assigned with this application, the disclosures of which are herein incorporated by reference.

An oligo-nucleotide/nucleoside for the purposes of the present invention is a mixed backbone oligomer having at least two nucleosides covalently bound by a non-phosphate linkage and forming a phosphorous containing covalent bond with a monomeric sub-unit as defined above. An oligo-nucleotide/nucleoside can have a plurality of nucleotides and nucleosides coupled through phosphorous containing and non-phosphorous containing linkages.

Methods of coupling monomeric sub-units of the invention include solution phase and solid phase chemistries. Representative solution phase techniques are described in U.S. Pat. No. 5,210,264, issued May 11, 1993 and commonly assigned with this invention. Representative solid phase techniques are those typically employed for DNA and RNA synthesis utilizing standard phosphoramidite chemistry. (see, e.g., Protocols For Oligonucleotides And Analogs, Agrawal, S., ed., Humana Press, Totowa, N.J., 1993.) A preferred synthetic solid phase synthesis utilizes phosphoramidites as activated phosphates. The phosphoramidites utilize $P^{III}$ chemistry. The intermediate phosphite compounds are subsequently oxidized to the $P^V$ state using known methods. This allows for synthesis of linkages including phosphodiester or phosphorothioate phosphate linkages depending upon oxidation conditions selected. Other phosphate linkages can also be generated. These include phosphorodithioates, phosphotriesters, alkyl phosphonates, phosphoroselenates and phosphoramidates.

For the purposes of this specification, in the context of the invention and in reference to the above Structure I, alkyl groups include but are not limited to substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methylpropyl, 2-methyl-4- ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched chain groups.

A number of substituent groups can be introduced into compounds of the invention in a protected (blocked) form and subsequently de-protected to form a final, desired compound. In general, protecting groups render chemical functionality inert to specific reaction conditions and can be appended to and removed from such functionality in a molecule without substantially damaging the remainder of the molecule. See, e.g., Greene and Wuts, *Protective Groups in Organic Synthesis*, 2d ed, John Wiley & Sons, New York, 1991. For example, amino groups can be protected as phthalimido groups or as 9-fluorenylmethoxycarbonyl (FMOC) groups and carboxyl groups can be protected as fluorenylmethyl groups. Representative hydroxyl protecting groups are described by Beaucage, et al., *Tetrahedron* 1992, 48, 2223. Preferred hydroxyl protecting groups are acid-labile, such as the trityl, monomethoxytrityl, dimethoxytrityl, and trimethoxytrityl groups.

Solid supports according to the invention include controlled pore glass (CPG), oxalyl-controlled pore glass (see, e.g., Alul, et al., *Nucleic Acids Research* 1991, 19, 1527), TentaGel Support—an aminopolyethyleneglycol derivatized support (see, e.g., Wright, et al., *Tetrahedron Letters* 1993, 34, 3373) or Poros—a copolymer of polystyrene/divinylbenzene. Many other solid supports are commercially available and amenable to the present invention.

An activated solid support in the context of the present invention is a solid support that has been derivatized with a functional group or treated with a reactive moiety such that the resulting activated solid support is chemically active towards reaction with a monomeric subunit or a nucleoside dimer of the invention.

Standard methods and techniques used to increase the coupling efficiency of oligonucleotide synthesis include activation of 3' and or 5' functional groups. Some commonly activated groups are phosphate and phosphite which give the corresponding activated phosphate and activated phosphite (see e.g., *Nucleic Acids in Chemistry and Biology*; Blackburn, G. M., Gait M. J., Eds. Chemical Synthesis; IL: New York, 1990, Chapter 3, p. 98). Many others are known and can be used herein.

Monomeric sub-units of the invention are coupled using linking moieties. Linking moieties include phosphodiester, phosphotriester, hydrogen phosphonate, alkylphosphonate, alkylphosphonothioate, arylphosphonothioate, phosphorothioate, phosphorodithioate, phosphoramidate, ketone, sulfone, carbonate and thioamidate. Alkylphosphonothioate linkages are disclosed in WO 94/02499. Other such moieties can also be employed.

In one aspect of the present invention 2'-F-5-alkyluridine (and the 5-halo analog) monomeric sub-units are prepared by first substituting the appropriate alkyl group on the 5-position of the nucleoside. In the case of a 5-halo group, 5-F, Cl, Br, and I uracils are available through Aldrich Chemical Company. Substitution of alkyl, alkenyl, and alkynyl groups at C-5 of uracil is disclosed in PCT application PCT/US92/10115, filed Nov. 24, 1992, and examples of alkyl substitutions are further disclosed by Manoharan, M., *Antisense Research and Applications*, Crooke and Lebleu, eds., CRC Press, Boca Raton, 1993.

5-Alkylated uridine is converted into the 2,2'-anhydro[1-(β-D-arabinofuranosyl)-5-alkyluridine] by treatment with diphenylcarbonate and sodium bicarbonate in DMF followed by purification. The 2,2'-anhydro[1-(β-D-arabinofuranosyl)- 5-alkyluridine] is further treated with HF/pyridine in an appropriate solvent, e.g. dioxane, to give 1-(2-fluoro-β-D-erythro-pentofuranosyl)-5-alkyluridine. This compound is converted into the DMT/amidite following standard methods and techniques to give 1-(5-O-dimethoxytrityl-2-fluoro-3-O-N,N-diisopropylamino-2-cyanoethylphosphite-β-D-erythro-pentofuranosyl)-5-alkyluridine. The 1-(5-O-dimethoxytrityl-2-fluoro-3-O-N,N-diisopropylamino-2-cyanoethylphosphite-β-D-erythro-pentofuranosyl)-5-alkyluridine is used as a monomeric sub-unit precursor in oligomeric compound synthesis.

Conversion of the 5-alkylated-2'-F-uridine to a 5-alkylated-2'-F-4-N-protected (e.g. benzoyl) cytidine is accomplished by known methods and techniques using 1,2,4-triazole. The 5-O-alkylated uridine is first protected at the 3' and 5' positions. This protection can be effected using acetic anhydride. 1,2,4-Triazole in an appropriate solvent (e.g. acetonitrile) with a base present (e.g. triethylamine) is treated with $POCl_3$ at low temperature. The protected 5-O-alkylated-2'-F-uridine is dissolved in an appropriate solvent and added to the solution containing the triazole/$POCl_3$. After sufficient time has passed and subsequent workup and purification the triazine-1-(3',5'-di-O-acetyl-2-fluoro-β-D-erythro-pentofuranosyl)-5-alkyluridine is obtained. This compound is converted into 5-alkyl-1-(2-fluoro-β-D-erythro-pentofuranosyl)-Cytosine by treatment with ammonia. The exocycloamino group is protected for example by treatment with benzoic anhydride in a suitable solvent e.g. pyridine.

This compound is converted into the DMT/amidite following standard methods and techniques to give 4-N-protected-5-alkyl-1-(2-fluoro-3-O-N,N-diisopropylamino-2-cyanoethylphosphite-5-O-dimethoxytrityl-β-D-erythro-pentofuranosyl)-Cytosine. The 4-N-protected-5-alkyl-1-(2-fluoro-3-O-N,N-diisopropylamino-2-cyanoethylphosphite-5-O-dimethoxytrityl-β-D-erythro-pentofuranosyl)-Cytosine is used as a monomeric sub-unit precursor in oligomeric compound synthesis.

The preparation of 5-substituted-2'-F-pyrimidines using more complicated groups than alkyl (e.g. halo or substituted $C_1$–$C_6$ alkyl, wherein said substitutions are halo, amino, hydroxyl, thiol, ether or thioether) for the substituent of the 5-position can require that the group be protected prior to preparing the anhydro compound using an appropriate protecting group. The overall synthesis of compounds with protected groups at the 5 position is identical to that described above for incorporation of one of these substituted alkyl groups in place of a saturated alkyl group.

In one aspect of the present invention, 2'-O-substituted-5-substituted uridine monomeric sub-units are prepared starting with 5-substituted uridine, synthesized as illustrated above. This compound is treated with dibutyltin oxide in an appropriate solvent, e.g. methanol, and purified. The resulting 1-(2',3'-di-O-butyltin-β-D-erythro-pentofuranosyl)-5-substituted uridine is treated with a haloalkyl, a protected haloalkylamino, or a haloalkylimidazo compound (e.g. iodopropane) in an appropriate solvent to give the respective 2'-O-substituent. Aralkyl and aryl groups can be used in place of the alkyl group.

In another aspect of the present invention 2'-O-substituted-5-substituted uridine monomeric sub-units are prepared using the 2, 2'-anhydro [1-(β-D-arabinofuranosyl)-5-alkyluridine procedures described except that to open the anhydro an alcohol is used e.g. phenol for phenyl substituent, or propanol for an O-propyl substituent.

The resulting compound is converted into the DMT/amidite following standard methods and techniques to give 1-(2-O-substituted-3-O-N,N-diisopropylamino-2-cyanoethylphosphite-5-O-dimethoxytrityl-β-D-erythro-pentofuranosyl)-5-substituted uridine. The DMT/amidite is used as a monomeric sub-unit precursor in oligomeric compound synthesis.

1-(2-O-substituted-5-dimethoxytrityl-β-D-erythro-pentofuranosyl)-5-substituted uridine is converted into the cytosine analog by known methods and techniques using 1,2,4-triazole. The 5-substituted-2'-O-substituted uridine is first protected at the 3' position using an appropriate protecting group e.g. acetic anhydride. The material is purified after workup. 1,2,4-Triazole in an appropriate solvent (e.g. acetonitrile) with a base present (e.g. triethylamine) is treated with $POCl_3$ at low temperature. The protected 5-substituted-2'-O-substituted-3'-O-protected uridine is dissolved in an appropriate solvent and added to the solution containing the triazole/$POCl_3$. After sufficient time has passed and subsequent workup and purification the 1-(2-O-substituted-3-O-acetyl-5-O-dimethoxytrityl-β-D-erythro-pentofuranosyl)-4-triazolo-5-substituted pyrimidine is obtained which is converted into the cytidine analog by treatment with ammonia. The exocycloamino group (N-4) is protected for example by treatment with benzoic anhydride in a suitable solvent like pyridine or DMF and further converted into the DMT/amidite as illustrated above. The resulting 1-(2-O-substituted-3-O-N,N-diisopropylamino-2-cyanoethylphosphite-5-O-dimethoxytrityl-β-D-erythro-pentofuranosyl)-4-N-benzoyl-5-substituted cytidine is used as a monomeric sub-unit precursor in oligomeric compound synthesis.

In other embodiments of the invention the 2-S analogs of the 2'-substituted-5-substituted pyrimidines are prepared. The 2'-O-substituted-2-thio-5-substituted uridine is prepared in one method by starting with a 2,3,5-tri-O-benzoyl ribose sugar and coupling to a 2-thio-5-substituted pyrimidine via a glycosylation step. The synthesis of varied 2-thio-5-substituted pyrimidines are disclosed in Vorbruggen, P., et.al., *Angew. Chem. Int.* Ed., 1969, 8, 976–977, and in Vorbruggen, P., et.al., *Chem. Ber.*, 1973, 106, 3039–3061. The 2,3,5-tri-O-benzoyl ribose sugar and a 5-substituted-2-thiouracil are dissolved in a suitable solvent and treated with N-O-Bis(trimethyl silyl)acetamide and trimethyl silyl triflate. The resulting 2,3,5-tri-O-benzoyl-2-thio-5-substituted uridine is deprotected using sodium methoxide in an appropriate solvent to give 2-thio-5-substituted uridine. The 2-thio-5-substituted uridine is dissolved in a suitable solvent and treated with dibutyltin oxide and tetrabutyl ammonium iodide followed by an alkyl halide e.g. methyl iodide, to give the 2'-O-substituted-2-thio-5-substituted uridine The 2'-O-substituted-2-thio-5-substituted uridine is converted into the DMT/amidite following standard methods and techniques to give 1-(2-O-substituted-3-O-N,N-diisopropylamino-2-cyanoethylphosphite-5-O-dimethoxytrityl-β-D-erythro-pentofuranosyl)-2-thio-5-substituted uridine. The DMT/amidite is used as a monomeric sub-unit precursor in oligomeric compound synthesis.

In still other embodiments of the invention the 2-S analogs of the 2'-F-5-substituted pyrimidines are prepared. One method of preparing 2'-F-2-Thio-5-substituted pyrimidines is to use a similar method to that used in the preparation of the 2'-F-2-substituted-5-substituted-pyrimidine. This involves doing selective protection of functional groups and forming the anhydro bond between S-2 and 2', analogous to the anhydro formed above between the O-2 and the 2'.

2,3,5-Tri-O-benzoyl-2-thio-5-methyl-uridine is formed via a glycosylation between 2,3,5-tri-O-benzoyl ribose and a 5-substituted-2-thiouridine. After deprotection with sodium methoxide in an appropriate solvent and purification the resulting 5-methyl-2-thiouridine is protected with DMT at the 5'-position using standard methods and techniques. Next, the 2'-position is protected with a t-butyl-dimethylsilyl group by treatment with t-butyldimethylsilyl chloride in an appropriate solvent.

The resulting 5'-O-dimethoxytrityl-3'-t-butyl-dimethylsilyl-5-substituted-2-thiouridine is dissolved in an appropriate solvent and treated with methanesulfonyl chloride to give the 5'-O-dimethoxytrityl-3'-t-butyl-dimethylsilyl-2'-methanesulfonyl-5-substituted-2-thiouridine. The 5'-O-dimethoxytrityl-3'-t-butyl-dimethylsilyl-2'-methanesulfonyl-5-substituted-2-thiouridine is further treated with sodium methoxide in an appropriate solvent to give the 5'-O-dimethoxytrityl-3'-t-butyl-dimethylsilyl-2-2'-thio anhydro-5-substituted-2-thiouridine. This compound is further treated with HF/pyridine in dioxane to give the 2'-Fluoro-3'-t-butyl-dimethylsilyl-5'-O-dimethoxytrityl-5-substituted-2-thiouridine.

The 2'-Fluoro-3'-t-butyl-dimethylsilyl-5'-O-dimethoxytrityl- 5-substituted-2-thiouridine is converted into the amidite using standard methods and techniques to give 1-(2-Fluoro-3-O-N,N-diisopropylamino-2-cyanoethylphosphite-5-O-dimethoxytrityl-β-D-erythro-pentofuranosyl)-2-thio-5-substituted uridine. The DMT/amidite is used as a monomeric sub-unit precursor in oligomeric compound synthesis.

The conversion of the 2'-Fluoro-3'-t-butyl-dimethylsilyl-5'-O-dimethoxytrityl-5-substituted-2-thiouridine into the cytidine analog is accomplished using the above procedures for conversion of the 1-(2-O-substituted-5-dimethoxytrityl-β-D-erythro-pentofuranosyl)-5-substituted uridine into its cytidine analog using the 1,2,4-triazole procedure. For the conversion of a 2-S compound this group must also be protected using an appropriate protecting group e.g. toluoyl.

In U.S. patent application entitled "Oligonucleotide Modulation of protein kinase C," Ser. No. 08/089,996, filed Jul. 9, 1995—also identified as attorney docket number ISIS-1154, commonly assigned with this application, the disclosure of which is herein incorporated by reference, gapped oligonucleotides (see, Dean, et.al., *J. Biol. Chem.*, 1994, 23, 16416) were synthesized and tested in a protein kinase C assay to determine their potency. One exemplary oligonucleotide having good potency is oligonucleotide SEQ ID NO: 1, which is a 20 mer deoxyphosphorothioate. This oligonucleotide gave approximately 80% reduction of the smaller transcript and over 90% reduction of the larger transcript in the above described assay.

In one embodiment of the present invention oligomeric compounds having at least one monomeric unit of structure I are synthesized and used to inhibit the synthesis of the PKC-α protein. Two oligonucleotides having similar sequences to SEQ ID NO: 1 were synthesized as oligonucleotide SEQ IN NO: 2, which is a fully modified phosphorothioate having 2'-fluoro at positions 1–6 and 15–20, and uracils in place of the thymines at positions 2, 3, 5, and 16–18, and as oligonucleotide SEQ IN NO: 3, which is a fully modified phosphorothioate having 2'-fluoro-5-methyluridine in place of the thymidines at positions 2, 3, 5, and 16–18, and further having 2'-fluoros at positions 1, 4, 6, 15, 19, and 20. These two oligonucleotides (SEQ IN NO: 2, SEQ IN NO: 3) were evaluated in the above assay and the results compared with that of SEQ IN NO: 1.

SEQ IN NO: 2 and SEQ IN NO: 3 exhibited about a 10 fold increase in potency relative to SEQ IN NO: 1. SEQ IN NO: 3 also showed a measurable increase in potency relative to SEQ IN NO: 2.

As expected from the above results the Tm's of these 3 oligonucleotides are in the order SEQ ID NO: 3 >SEQ ID NO: 2>SEQ ID NO: 1.

| SEQ ID NO | Sequence | Tm | ISIS# |
|---|---|---|---|
| 1 | GTT CTC GCT GGT GAG TTT CA | 52.1° C. | 3521 |
| 2 | GUU CUC GCT GGT GAG UUU CA | 64.9° C. | 8469-2 |
| 3 | GUU CUC GCT GGT GAG UUU CA | 69.0° C. | 8469-3 |

EXAMPLE 1

2,2'-anhydro[1-(β-D-arabinofuranosyl)-5-methyluridine]

5-Methyluridine (ribosylthymine, commercially available through Yamasa, Choshi, Japan) (72.0 g, 0.279 mol), diphenylcarbonate (90.0 g, 0.420 mol) and sodium bicarbonate (2.0 g, 0.024 mol) were added to dimethylformamide (300 mL). The mixture was heated to reflux with stirring allowing the resulting carbon dioxide gas to evolve in a controlled manner. After 1 hour, the slightly darkened solution was concentrated under reduced pressure. The resulting syrup was poured into stirred diethyl ether (2.5 L). The product formed a gum. The ether was decanted and the residue was dissolved in a minimum amount of methanol (ca 400 Ml). The solution was poured into fresh ether as above (2.5 L) to give a stiff gum. The ether was decanted and the gum was dried in a vacuum oven (60° C. at 1 mm Hg for 24 h) to give a solid which was crushed to a light tan powder (57 g, 85% crude yield). NMR was consistent with structure and contamination with phenol and its sodium salt (ca 5%). The material was used as is for ring opening. It can be purified further by column chromatography using a gradient of methanol in ethyl acetate (10–25%) to give a white solid, mp 222–4° C.

EXAMPLE 2

1-(2-fluoro-β-D-erythro-pentofuranosyl)-5-methyluridine 2,2'-Anhydro[1-(β-D-arabinofuranosyl)-5-methyluridine] (71 g, 0.32 mmol) and dioxane (700 mL) are placed in a 2 liter stainless steel bomb and HF/pyridine (100 g, 70%) was added. The mixture was heated for 16 hours at 120–125° C. and then cooled in an ice bath. The bomb was opened and the mixture was poured onto 3 liters of ice. To this mixture was added cautiously sodium hydrogen carbonate (300 g) and saturated sodium bicarbonate solution (400 mL). The mixture was filtered and the filter cake was washed with water (2×100 mL) and methanol (2×500 mL). The water and methanol washes were concentrated to dryness in vacuo. Methanol (200 mL) and coarse silica gel (80 g) were added to the residue and the mixture was concentrated to dryness in vacuo. The resulting material was concentrated onto the silica gel and purified by silica gel column chromatography using a gradient of ethyl acetate and methanol (100:0 to 85:15). Pooling and concentration of the product fractions gave 36.9 g (51%, 2 step yield) of the title compound.

Also isolated from this reaction was 1-(2-phenyl-β-D-erythro-pentofuranosyl)-5-methyluridine (10.3 g). This material is formed from the phenol and its sodium salt from the anhydro reaction above when the bomb reaction is carried out on impure material. When The anhydro material is purified this product is not formed. The formed 1-(2-phenyl-β-D-erythro-pentofuranosyl)-5-methyluridine was converted into its DMT/phosphoramidite using the same reaction conditions as for the 2'-Fluoro material.

EXAMPLE 3

1-(5-O-Dimethoxytrityl-2-fluoro-β-D-erythro-pentofuranosyl)-5-methyluridine 1-(2-fluoro-β-D-erythro-pentofuranosyl)-5-methyluridine (31.15 g, 0.12 mol) was suspended in pyridine (150 mL) and dimethoxytrityl chloride (44.62 g, 0.12 mol) was added. The mixture was stirred in a closed flask for 2 hours and then methanol (30 mL) was added. The mixture was concentrated in vacuo and the resulting residue was partitioned between saturated bicarbonate solution (500 mL) and ethyl acetate (3×500 ml). The ethyl acetate fractions were pooled and dried over magnesium sulfate, filtered and concentrated in vacuo to a thick oil. The oil was dissolved in dichloromethane (100 mL), applied to a silica gel column and eluted with ethyl acetate:hexane:triethylamine, 60/39/1 increasing to 75/24/1. The product fractions were pooled and concentrated in vacuo to give 59.9 g (89%) of the title compound as a foam.

EXAMPLE 4

1-(5-O-Dimethoxytrityl-2-fluoro-3-O-N,N-diisopropylamino-2-cyanoethylphosphite-β-D-erythro-pentofuranosyl)-5-methyluridine 1-(5-O-Dimethoxytrityl-2-fluoro-β-D-erythro-pentofuranosyl)-5-methyluridine (59.8 g, 0.106 mol) was dissolved in dichloromethane and 2-cyanoethyl N,N,N',N'-tetraisopropyl-phosphorodiamidite (46.9 mL, 0.148 mol) and diisopropylamine tetrazolide (5.46 g, 0.3 eq.) was added. The mixture was stirred for 16 hours. The mixture was washed with saturated sodium bicarbonate (1 L) and the bicarbonate solution was back extracted with dichloromethane (500 mL). The combined organic layers were washed with brine (1 L) and the brine was back extracted with dichloromethane (100 mL). The combined organic layers were dried over sodium sulfate, filtered, and concentrated to a vol of about 200 mL. The resulting material was purified by silica gel column chromatography using hexane/ethyl acetate/triethyl amine 60/40/1. The product fractions were concentrated in vacuo, dissolved in acetonitrile (500 ml), filtered, concentrated in vacuo, and dried to a foam. The foam was chopped and dried for 24 hour to a constant weight to give 68.2 g (84%) of the title compound. 1H NMR: (CDCl$_3$) δ 0.9–1.4 (m, 14 H, 4×CH$_3$, 2×CH), 2.3–2.4 (t, 1 H, CH$_2$CN), 2.6–2.7 (t, 1 H, CH$_2$CN), 3.3–3.8 (m, 13 H, 2×CH$_3$OAr, 5' CH$_2$, CH$_2$OP, C-5 CH$_3$), 4.2–4.3 (m, 1 H, 4'), 4.35–5.0 (m, 1 H, 3'), 4.9–5.2 (m, 1 H, 2'), 6.0–6.1 (dd, 1 H, 1'), 6.8–7.4 (m, 13 H, DMT), 7.5–7.6 (d, 1 H, C-6), 8.8 (bs, 1 H, NH). $^{31}$P NMR (CDCl$_3$); 151.468, 151.609, 151.790, 151.904.

EXAMPLE 5

1-(3',5'-di-O-acetyl-2-fluoro-β-D-erythro-pentofuranosyl)-5-methyluridine 1-(2-fluoro-β-D-erythro-pentofuranosyl)-5-methyluridine (22.4 g, 92 mmol, 85% purity), prepared as per the procedure of Example 2, was azeotroped with pyridine (2×150 mL) and dissolved in pyridine (250 mL). Acetic anhydride (55 mL, 0.58 mol) was added and the mixture was stirred for 16 hours. Methanol (50 mL) was added and stirring was continued for 30 minutes. The mixture was evaporated to a syrup. The syrup was dissolved in a minimum amount of methanol and loaded onto a silica gel column. Hexane/ethyl acetate, 1:1, was used to elute the product fractions. Purification gave 19.0 g (74%) of the title compound.

EXAMPLE 6

4-Triazine-1-(3',5'-di-O-acetyl-2-fluoro-β-D-erythro-pentofuranosyl)-5-methyluridine 1,2,4-Triazole (106 g, 1.53 mol) was dissolved in acetonitrile (150 mL) followed by triethylamine (257 mL, 1.84 mol). The mixture was cooled to between 0 and 10° C. using an ice bath. $POCl_3$ (34.5 mL, 0.375 mol) was added slowly via addition funnel and the mixture was stirred for an additional 45 minutes. In a separate flask, 1-(3',5'-Di-O-acetyl-2-fluoro-β-D-erythro-pentofuranosyl)-5-methyluridine (56.9 g, 0.144 mol) was dissolved in acetonitrile (150 mL). The solution containing the 1-(3',5'-Di-O-acetyl-2-fluoro-β-D-erythro-pentofuranosyl)-5-methyluridine was added via cannula to the triazole solution slowly. The ice bath was removed and the reaction mixture was allowed to warm to room temperature for 1 hour. The acetonitrile was removed in vacuo and the residue was partitioned between saturated sodium bicarbonate solution (400 mL) and dichloromethane (4×400 mL). The organic layers were combined and concentrated in vacuo. The resulting residue was dissolved in ethyl acetate (200 mL) and started to precipitate a solid. Hexanes (300 mL) was added and additional solid precipitated. The solid was collected by filtration and washed with hexanes (2×200 mL) and dried in vacuo to give 63.5 g which was used as is without further purification.

EXAMPLE 7

5-methyl-1-(2-fluoro-β-D-erythro-pentofuranosyl)-Cytosine

4-Triazine-1-(3',5'-di-O-acetyl-2-fluoro-β-D-erythro-pentofuranosyl)-Thymine (75.5 g, .198 mol) was dissolved in ammonia (400 mL) in a stainless steel bomb and sealed overnight. The bomb was cooled and opened and the ammonia was evaporated. Methanol was added to transfer the material to a flask and about 10 volumes of ethyl ether was added. The mixture was stirred for 10 minutes and then filtered. The solid was washed with ethyl ether and dried to give 51.7 g (86%) of the title compound.

EXAMPLE 8

4-N-Benzoyl-5-methyl-1-(2-fluoro-β-D-erythro-pentofuranosyl)-Cytosine 5-methyl-1-(2-fluoro-β-D-erythro-pentofuranosyl)-Cytosine (54.6 g, 0.21 mol) was suspended in pyridine (700 mL) and benzoic anhydride (70 g, 0.309 mol) was added. The mixture was stirred for 48 hours at room temperature. The pyridine was removed by evaporation and methanol (800 mL) was added and the mixture was stirred. A precipitate formed which was filtered, washed with methanol (4×50mL), washed with ether (3×100 mL), and dried in a vacuum oven at 45° C. to give 40.5 g of the title compound. The filtrate was concentrated in vacuo and treated with saturated methanolic ammonia in a bomb overnight at room temperature. The mixture was concentrated in vacuo and the resulting oil was purified by silica gel column chromatography. The recycled starting material was again treated as above to give an additional 4.9 g of the title compound to give a combined 45.4 g (61%) of the title compound.

EXAMPLE 9

4-N-Benzoyl-5-methyl-1-(2-fluoro-5-O-dimethoxytrityl-β-D-erythro-pentofuranosyl)-Cytosine 4-N-Benzoyl-5-methyl-1-(2-fluoro-β-D-erythro-pentofuranosyl)-Cytosine (45.3 g, 0.124 mol) was dissolved in 250 ml dry pyridine and dimethoxytrityl chloride (46.4 g, 0.137 mol) was added. The reaction mixture was stirred at room temperature for 90 minutes and methanol (20 mL) was added. The mixture was concentrated in vacuo and partitioned between ethyl acetate (2×1 L) and saturated sodium bicarbonate (1 L). The ethyl acetate layers were combined, dried over magnesium sulfate and evaporated in vacuo. The resulting oil was dissolved in dichloromethane (200 mL) and purified by silica gel column chromatography using ethyl acetate/hexane/triethyl amine 50:50:1. The product fractions were pooled concentrated in vacuo dried to give 63.6 g (76.6%) of the title compound.

EXAMPLE 10

4-N-Benzoyl-5-methyl-1-(2-fluoro-3-O-N,N-diisopropylamino-2-cyanoethylphosphite-5-O-dimethoxytrityl-β-D-erythro-pentofuranosyl)-Cytosine 4-N-Benzoyl-5-methyl-1-(2-fluoro-5-O-dimethoxytrityl-β-D-erythro-pentofuranosyl)-Cytosine (61.8 g, 92.8 mmol) was stirred with dichloromethane (300 mL), 2-cyanoethyl N,N,N',N'-tetraisopropylphosphorodiamidite (40.9 mL, 0.130 mol) and diisopropylamine tetrazolide (4.76 g, 0.3 eq.) at room temperature for 17 hours. The mixture was washed with saturated sodium bicarbonate (1 L) and the bicarbonate solution was back extracted with dichloromethane (500 mL). The combined organic layers were washed with brine (1 L) and the brine was back extracted with dichloromethane (100 mL). The combined organic layers were dried over sodium sulfate, filtered, and concentrated to a vol of about 200 mL. The resulting material was purified by silica gel column chromatography using hexane/ethyl acetate/triethyl amine 60/40/1. The product fractions were concentrated in vacuo, dissolved in acetonitrile (500 ml), filtered, concentrated in vacuo, and dried to a foam. The foam was chopped and dried for 24 hours to a constant weight to give 72.4 g (90%) of the title compound. 1H NMR: ($CDCl_3$) δ 1.17–1.3 (m, 12 H, 4×$CH_3$), 1.5–1.6 (m, 2 H, 2×CH), 2.3–2.4 (t, 1 H, $CH_2CN$), 2.6–2.7 (t, 1 H, $CH_2CN$), 3.3–3.9 (m, 13 H, 2×$CH_3OAr$, 5' $CH_2$, $CH_2OP$, C-5 $CH_3$), 4.2–4.3 (m, 1 H, 4'), 4.3–4.7 (m, 1 H, 3'), 5.0–5.2 (m, 1 H, 2'), 6.0–6.2 (dd, 1 H, 1'), 6.8–6.9 (m, 4 H, DMT), 7.2–7.6 (m, 13 H, DMT, Bz), 7.82–7.86 (d, 1 H, C-6), 8.2–8.3 (d, 2 H, Bz). $^{31}P$ NMR ($CDCl_3$); bs, 151.706; bs, 151.941.

EXAMPLE 11

1-(2,3-di-O-Butyltin-β-D-erythro-Pentofuranosyl)-5-Methyluridine

5-Methyl uridine (7.8 g, 30.2 mmol) and dibutyltin oxide (7.7 g, 30.9 mmol) were suspended in methanol (150 mL)

and heated to reflux for 16 hours. The reaction mixture was cooled to room temperature, filtered, and the solid washed with methanol (2×150 mL). The resulting solid was dried to give 12.2 g (80.3%) of the title compound. This material was used without further purification in subsequent reactions. NMR was consistent with structure.

EXAMPLE 12

1-(2-O-Propyl-β-D-erythro-Pentofuranosyl)-5-Methyluridine 1-(2,3-di-O-butyltin-β-D-erythro-pentofuranosyl)-5-methyluridine (5.0 g, 10.2 mmol) and iodopropane (14.7 g, 72.3 mmol) were stirred in DMF at 100° C. for 2 days. The reaction mixture was cooled to room temperature and filtered and concentrated. The residual DMF was coevaporated with acetonitrile. After drying the residue there was obtained 2.40 g (78%) of the title compound and the 3'-O-propyl isomer as a crude mixture. This material was used without further purification in subsequent reactions.

EXAMPLE 13

1-(2-O-Propyl-5-O-Dimethoxytrityl-β-D-erythro-Pentofuranosyl)-5-Methyluridine 1-(2-O-Propyl-β-D-erythro-pentofuranosyl)-5-methyluridine and the 3'-O-propyl isomer as a crude mixture (2.4 g, 8.4 mmol) was coevaporated with pyridine (2×40 mL) and dissolved in pyridine (60 mL). The solution was stirred at room temperature under argon for 15 minutes and dimethoxytrityl chloride (4.27 g, 12.6 mmol) was added. The mixture was checked periodically by tlc and at 3 hours was completed. Methanol (10 mL) was added and the mixture was stirred for 10 minutes. The reaction mixture was concentrated in vacuo and the resulting residue purified by silica gel column chromatography using 60:40 hexane/ethyl acetate with 1% triethylamine used throughout. The pooling and concentration of appropriate fractions gave 1.32 g (26%) of the title compound.

EXAMPLE 14

1-(2-O-Propyl-3-O-N,N-Diisopropylamino-2-Cyanoethylphosphite-5-O-Dimethoxytrityl-β-D-erythro-Pentofuranosyl)-5-Methyluridine 1-(2-O-Propyl-5-O-dimethoxytrityl-β-D-erythro-pentofuranosyl)-5-methyluridine (50.0 g, 86 mmol), 2-cyano-ethyl-N,N,N',N'-tetra-isopropylphosphorodiamidite (38 mL, 120 mmol), and diisopropylamine tetrazolide (4.45 g, 25.8 mmol) were dissolved in dichloromethane (500 mL) and stirred at room temperature for 40 hours. The reaction mixture was washed with saturated sodium bicarbonate solution (2×400 mL) and brine (1×400 mL). The aqueous layers were back extracted with dichloromethane. The dichloromethane layers were combined, dried over sodium sulfate, filtered, and concentrated in vacuo. The resultant residue was purified by silica gel column chromatography using ethyl acetate/hexane 40:60 and 1% triethylamine. The appropriate fractions were pooled, concentrated, and dried under high vacuum to give 43 g (67%).

EXAMPLE 15

1-(2-O-Propyl-3-O-Acetyl-5-O-Dimethoxytrityl-β-D-erythro-Pentofuranosyl)-5-Methyluridine 1-(2-O-Propyl-5-dimethoxytrityl-β-D-erythro-pentofuranosyl)-5-methyluridine (10.0 g, 16.6 mmol) was dissolved in pyridine (50 mL) and acetic anhydride (4.7 ml, 52.7 mmol) was added. The reaction mixture was stirred for 18 hours and excess acetic anhydride was neutralized with methanol (10 mL). The mixture was concentrated in vacuo and the resulting residue dissolved in ethyl acetate (150 mL). The ethyl acetate was washed with saturated NaHCO$_3$ (150 mL) and the saturated NaHCO$_3$ wash was back extracted with ethyl acetate (50 mL). The ethyl acetate layers were combined and concentrated in vacuo to yield a white foam 11.3 g. The crude yield was greater than 100% and the NMR was consistent with the expected structure of the title compound. This material was used without further purification in subsequent reactions.

EXAMPLE 16

1-(2-O-Propyl-3-O-Acetyl-5-O-Dimethoxytrityl-β-D-erythro-Pentofuranosyl)-4-Triazolo-5-Methylpyrimidine Triazole (10.5 g, 152 mmol) was dissolved in acetonitrile (120 ml) and triethylamine (23 mL) with stirring under anhydrous conditions. The resulting solution was cooled in a dry ice acetone bath and phosphorous oxychloride (3.9 mL, 41 mmol) was added slowly over a period of 5 minutes. The mixture was stirred for an additional 10 minutes becoming a thin slurry indicative of product formation. 1-(2-O-Propyl-3-O-acetyl-5-O-dimethoxytrityl-β-D-erythro-pentofuranosyl)-5-methyluridine (11.2 g, 165mmol) was dissolved in acetonitrile (150 mL) and added to the slurry above, maintaining dry ice acetone bath temperatures. The reaction mixture was stirred for 30 minutes and then allowed to warm to room temperature and stirred for an additional 2 hours. The mixture was placed in a freezer at 0° C. for 18 hours and then removed and allowed to warm to room temperature. Tlc in ethyl acetate/hexane 1:1 of the mixture showed complete conversion of the starting material. The reaction mixture was concentrated in vacuo and redissolved in ethyl acetate (300 mL) and extracted with saturated sodium bicarbonate solution (2×400 mL) and brine (400 mL). The aqueous layers were back extracted with ethyl acetate (200 mL). The ethyl acetate layers were combined, dried over sodium sulfate, and concentrated in vacuo. The crude yield was 11.3 g (95%). The NMR was consistent with the expected structure of the title compound. This material was used without further purification in subsequent reactions.

EXAMPLE 17

1-(2-O-Propyl-5-O-Dimethoxytrityl-β-D-erythro-Pentofuranosyl)-5-Methylcytidine 1-(2-O-Propyl-3-O-acetyl-5-O-dimethoxytrityl-β-D-erythro-pentofuranosyl)-4-triazolo-5-methylpyrimidine (11.2 g, 16.1 mmol) was dissolved in liquid ammonia (50 mL) in a 100 mL bomb at dry ice acetone temperatures. The bomb was allowed to warm to room temperature for 18 hours and then recooled to dry ice acetone temperatures. The bomb contents were transferred to a beaker and methanol (50 mL) was added. The mixture was allowed to evaporate to near dryness. Ethyl acetate (300 mL) was added and some solid was filtered off prior to washing with saturated sodium bicarbonate solution (2×250 mL). The ethyl acetate layers were dried over sodium sulfate, filtered, combined with the solid previously filtered off, and concentrated in vacuo to give 10.1 g of material. The crude yield was greater than 100% and the NMR was consistent with the expected structure of the title compound. This material was used without further purification in subsequent reactions.

EXAMPLE 18

1-(2-O-Propyl-5-O-Dimethoxytrityl-β-D-erythro-Pentofuranosyl)-4-N-Benzoyl-5-Methylcytidine 1-(2-O-Propyl-5-O-dimethoxytrityl-β-D-erythro-pentofuranosyl)-5-methylcytidine (7.28 g, 10.1 mmol) and benzoic anhydride (4.5 g, 20 mmol) were dissolved in DMF (60 mL) and stirred at room temperature for 18 hours. The reaction mixture was concentrated in vacuo and redissolved in ethyl acetate (300 mL). The ethyl acetate solution was washed with saturated sodium bicarbonate solution (2×400 mL), dried over sodium sulfate, filtered, and concentrated in vacuo. The residue was purified by silica gel column chromatography using ethyl acetate/hexane 1:2 and 1% triethylamine. The appropriate fractions were pooled, concentrated, and dried under high vacuum to give 5.1 g (59% for 4 steps starting with the 1-(2-O-Propyl-dimethoxytrityl-β-D-erythro-pentofuranosyl)-5-methyluridine).

EXAMPLE 19

1-(2-O-Propyl-3-O-N,N-Diisopropylamino-2-Cyanoethylphosphite-5-O-Dimethoxytrityl-β-D-erythro-Pentofuranosyl)-4-N-Benzoyl-5-Methylcytidine 1-(2-O-Propyl-5-O-dimethoxytrityl-β-D-erythro-pentofuranosyl)-4-N-benzoyl-5-methylcytidine (5.0 g, 7 mmol), 2-cyanoethyl-N,N,N',N'-tetra-isopropylphosphorodiamidite (3.6 mL, 11.3 mmol), and diisopropylaminotetrazolide (0.42 g, 2.4 mmol) were dissolved in dichloromethane (80 mL) and stirred at room temperature for 40 hours. The reaction mixture was washed with saturated sodium bicarbonate solution (2×40 mL) and brine (1×40 mL). The aqueous layers were back extracted with dichloromethane. The dichloromethane layers were combined, dried over sodium sulfate, filtered, and concentrated in vacuo. The resultant residue was purified by silica gel column chromatography using ethyl acetate/hexane 40:60 and 1% triethylamine. The appropriate fractions were pooled, concentrated, and dried under high vacuum to give 7.3 g (98%).

EXAMPLE 20

2'-O-Methyl-5-methyluridine

Procedure 1:

Crude 2,2'-anhydro-5-methyluridine (10.0 g, 0.0416 mol) was dissolved in methanol (80 mL) in a stainless steel bomb (100 mL capacity). Trimethyl borate (5.6 mL, 0.049 mol) was added (Note 1). The bomb was sealed and placed in an oil bath at 150° C. which generated a pressure of about 5 atm. After 40 h, the bomb was cooled in ice, opened and the contents concentrated under reduced pressure to a tan foam, 12 g. NMR of the crude was consistent with the product contaminated with impurities in the starting material and a trace of thymine and starting material (Note 2). The crude product was used as is for the next step.

Note that Trialkyl borates can be conveniently generated by adding solutions (eg 1 M in THF) of borane to the desired alcohol and allowing the resulting hydrogen gas to evolve.) Also note that the nucleoside can be purified at this point by column chromatography using a gradient of methanol in ethyl acetate (0–10%) and crystallizing the product from absolute ethanol to give white needles, mp 192–193° (mp 197–198°). Literature reference for the melting point of this compound is contained in E. Ootsuka, H. Inoue, Japanese Patent 89–85456, Apr. 4, 1989.

Procedure 2:

Pure 2,2'-anhydro-5-methyluridine (1.0 g, 4.16 mmol) and trimethylborate (0.56 mL, 4.9 mmol) was dissolved in methanol (20 mL) in a stainless steel bomb (100 mL). The bomb was placed in an oil bath at 150° C. After 80 h, TLC indicating the reaction to be mostly complete. The solvent was removed yielding a white foam. NMR indicated product to starting material ratio of 93:7 with no other impurities noted. The residue was purified by silica gel column chromatography using a methanol gradient in ethyl acetate (0–10%) yielding 850 mg (75%) of pure product and 250 mg of still contaminated product. An analytically pure sample was prepared for NMR. $^1$H NMR (DMSO-$d_6$): δ 1.79 (s, 3H, 5-CH$_3$), 3.35 (s, 3H, OCH$_3$), 3.5–3.7 (m, 2H, H-5'), 3.7–3.9 (m, 2H, H-3',4'), 4.15 (m, 1H, H-2'), 5.17 (m, 2H, 3',5'—OH), 5.87 (d, J=5 Hz, 1H, H-1'), 7.80 (s, 1H, H-6), 11.37 (br s, 1H, N—H).

Anal. Calcd for $C_{11}H_{16}N_2O_6$ (272.26): C, 48.52; H, 5.92; N, 10.29. Found: C, 48.56; H, 5.88; N, 10.22.

Procedure 3:

The same as described for procedure 2 except 30 mg of sodium bicarbonate was added to the reaction (to match the sodium content of the crude anhydro) which allowed the reaction to be complete in 24 h. Ammonium chloride (50 mg) was added to neutralize the base and the solution was stripped to dryness. NMR of the crude indicated three minor nucleoside impurities (total about 6%). After a similar column and then crystallizing the residue from methanol/ethyl acetate, there remained 850 mg of first crop material and 120 mg of second crop material both with 2–3% of unknown nucleoside impurities for a still contaminated yield of 85%.

EXAMPLE 21

5'-O-Dimethoxytriphenylmethyl-2'-O-methyl-5-methyluridine

Crude 2'-O-methyl-5-methyl uridine (12 g) was coevaporated in pyridine (2×50 mL) and dissolved in dry pyridine (50 mL). Dimethoxytriphenylmethyl chloride (18.1 g, 0.054 mol) was added. the flask was stoppered and allowed to stand for 45 min at room temperature. Methanol (10 mL) was added to quench the reaction and the solution was concentrated under reduced pressure to an oil. The residue was partitioned between ethyl acetate (2×400 mL) and saturated sodium bicarbonate solution (500 mL). The organic layers were combined, dried (sodium sulfate), filtered and concentrated to a yellow foam. The foam was dissolved in methylene chloride (60 mL) and put onto a silica gel column (300 g) and eluted with ethyl acetate-hexanes-triethylamine, 60:40:1. The product containing fractions were combined, concentrated and coevaporated with dry acetonitrile (2×50 mL). The resulting residue was dried at 1 mm Hg for 24 h to a crisp white foam, 17.0 g (60.4% in three steps from 5-methyluridine).

EXAMPLE 22

2,3,5-Tri-O-Benzoyl-2-Thio-5-Methyl Uridine

In a 250 ml 3 neck round bottomed flask 1-O-acetyl-2,3,5 tri-O-benzoyl ribose (0.500 g, 1 mmol) and 5-methyl-2-thio-uracil (0.156 g, 1.1 mmol) was dried under vacuum overnight. These components were dissolved in 10 mL of dry acetonitrile and heated to 80° C. To this warm solution was added N-O-Bis(trimethyl silyl)acetamide (0.509 g, 2.5 mmol) and the reaction stirred for 1 hr at 80° C. The reaction mixture was removed from the heat and allowed to cool to room temperature, and trimethyl silyl triflate (0.334 g, 1.5 mmol) was added dropwise. The reaction mixture was then heated to 50° C. and stirred for 4 hours. The reaction mixture was checked by TLC using ethyl acetate/hexane 1:1, which showed the reaction had gone to completion. The solution was cooled to room temperature and partitioned between 50 mL of dichloromethane and 50 mL of saturated sodium bicarbonate solution. The aqueous phase was extracted two more times with dichloromethane and the organic layers combined, dried with magnesium sulfate and concentrated to a pale yellow foam. This foam was used without further purification.

EXAMPLE 23

2-Thio-5-Methyl Uridine

The crude 2,3,5-tri-O-benzoyl-2-thio-5-methyl uridine (20 g, 37 mmoles) was dissolved in 500 mL of methanol. To this solution was added sodium methoxide (2.0 g, 37 mmoles) and the reaction stirred for 2 hours. The reaction was checked by TLC using ethyl acetate/hexane 1:1 and ethyl acetate/methanol 9:1, which showed the reaction had gone to completion. Dowex 50 H$^+$ resin was added until the solution was neutral by pH paper and the resin filtered. The resin was then washed with 100 ml of additional methanol and the combined filtrates were concentrated to give the title compound 8.5 g, (84%) as a pale yellow foam.

EXAMPLE 24

2'-O-Methyl-5-Methyl-2-Thiouridine

To a stirred solution of 5-methyl-2-thiouridine (0.500 g, 1.8 mmol) in DMF (10 ml) is added dibutyltin oxide (0.500 g, 2.0 mmol), tetrabutyl ammonium iodide (0.738 g, 2 mmol), and methyl iodide (1.022 g, 7.2 mmol). The reaction flask is sealed and heated at 50° C. for 16 hours. The mixture is cooled and another portion of methyl iodide is added (1.022 g, 7.2 mmol) and the reaction heated for an additional 16 hours. At the end of this time, the reaction mixture is cooled to room temperature and diluted with methylene chloride and chromatographed using a methylene chloride/methanol gradient. The appropriate fractions are collected and concentrated to give 2'-O-methyl-5-methyl-2-thiouridine.

EXAMPLE 25

2'-O-propyl 5-methyl-2-thiouridine

The title compound is prepared as per the procedures of Example 24 by substituting propyl iodide (1.22 g, 7.2 mmoles) in place of methyl iodide.

EXAMPLE 26

2'-O-phthalimidopropyl-5-methyl-2-thiouridine

The title compound was prepared as per the procedures of Example 24 by substituting bromo-propyl phthalimide (0.67 g, 2.5 mmoles) in place of methyl iodide, with an additional (0.300 g) added on the second day.

EXAMPLE 27

5'-O-Dimethoxytrityl-2'-O-Propylamine-5-Methyl-2-Thiouridine

2'-O-Phthalimidopropyl-5-methyl-2-thiouridine (2.6 g, 3.6 mmol) was dissolved in dry pyridine and co-evaporated twice. The resulting foam was dissolved in 25 mL of dry pyridine and dimethoxy-trityl chloride (1.8 g, 5.5 mmol) was added followed by 4,4-dimethylaminopyridine (0.050 g, 0.4 mmol). The reaction was allowed to stir overnight at room temperature. To the reaction mixture was added 1 mL of methanol. The solution was partitioned between 75 mL of saturated sodium bicarbonate and 50 mL of chloroform. The aqueous layer was extracted with two additional portions of chloroform and the organic layers combined and dried with magnesium sulfate. After removal of the drying agent via filtration the filtrate was concentrated to an orange oil and purified by silica gel column chromatography using methanol/chloroform gradient with 0.5% pyridine added to neutralize the silica gel.

EXAMPLE 28

5'-O-Dimethoxytrityl-2'-O-Propylamine-5-Methyl-2S-toluoyl-2-Thiouridine

5'-O-Dimethoxytrityl-2'-O-propylamine-5-methyl-2-thiouridine (1 g, 1.6 mmol) was dissolved in DMF and cooled to 0° C. To this solution was added triethyl amine (0.300 g, 3 m.mol) followed by toluoyl chloride (0.300 g, 1.92 mmol) dropwise over 5 minutes. The reaction was then allowed to warm to room temperature and stirred overnight, when complete the reaction was quenched with methanol and concentrated to an oil. The oil was then partitioned between 250 mL of a solution of saturated sodium bicarbonate/chloroform 1:1. The aqueous layer was extracted with two additional, 75 mL portions of chloroform, and the organic layers were dried and concentrated to an oil. The protected nucleoside was purified by silica gel column chromatography using a hexane/ethyl acetate gradient. The desired product was collected as a mixture of N-3 toluoyl and S-2 Toluoyl compounds. This mixture was used as is for the phosphytilation procedure.

EXAMPLE 29

5'-O-Dimethoxytrityl-2'-O-Propylamine-3'-O-[(N,N-diisopropylamino)-2-cyanoethoxyphosphite]-5-Methyl-2-S-toluoyl-2-Thiouridine To a solution of 5'-O-dimethoxytrityl-2'-O-propylamine-5-methyl-2-S-toluoyl-2-thiouridine (16.01 g, 22 mmol) and diisopropylethylamine (10 ml) in THF (200 ml), at 0° C., is added chloro-β-cyanoethoxy-N,N-diisopropylaminophosphine (5.6 ml, 25 mmol). The reaction mixture was stirred at room temperature for 20 hours. The reaction was concentrated and the residue purified by silica gel column chromatography. Elution with an ethyl acetate/hexane gradient while maintaining 1% triethylamine, pooling of appropriate fractions and evaporation will give the title compound.

EXAMPLE 30

2'-O-Aminopropyl-5-Methyl-2-Thiouridine

2'-O-Phthalimidopropyl-5-methyl-2-thiouridine (5.0 g, 15.8 mmol) is dissolved in 100 ml methanol in a 500 ml flask. Hydrazine (2.02 g, 63.2 mmol) is added and the mixture is heated to reflux (60–65° C.) with stirring for 14 hours. The solvent is evaporated in vacuo and the residue is dissolved in dichloromethane (150 ml) and extracted twice with an equal volume NH$_4$OH. The organic layer is evaporated to yield the crude product. NMR is used to assay product purity. The product is used in subsequent reactions without further purification.

EXAMPLE 31

2'-0-Trifluoroacetylaminopropyl-5-Methyl-2-Thiouridine

2'-O-Aminopropyl-5-methyl-2-thiouridine is dissolved in MeOH and 5 equivalents of triethylamine are added followed by 10 equivalents of ethyl trifluoroacetate. The title compound is isolated after purification.

EXAMPLE 32

2'-O-Trifluoroacetylaminopropyl-5'-O-Dimethoxytrityl-5-Methyl-2-Thiouridine

2'-O-Trifluoroacetylaminopropyl-5-methyl-2-thiouridine (2.5 g, 3.6 mmol) is dissolved in dry pyridine and co-evaporated twice. The resulting yellow foam is dissolved in 25 mL of dry pyridine and dimethoxytrityl chloride (1.8 g, 5.5 mmol) is added followed by 4,4-dimethylaminopyridine (0.050 g, 0.4 mmol). The reaction is allowed to stir overnight at room temperature. To the reaction mixture is added 1 mL of methanol. The solution is partitioned between 75 mL of saturated sodium bicarbonate and 50 mL of chloroform. The aqueous layer is extracted with two additional portions of chloroform and the organic layers combined and dried with magnesium sulfate. After removal of the drying agent via filtration the filtrate is concentrated to an oil and purified by silica gel column chromatography using methanol/chloroform gradient with 0.5% pyridine added to neutralize the silica gel to give the title compound.

EXAMPLE 33

2'-O-Trifluoroacetylaminopropyl-3'-O-[(N,N-diisopropylamino)-2-cyanoethoxyphosphite]-5'-O-Dimethoxytrityl-5-Methyl-2-Thiouridine The title compound is prepared as per the procedure of Example 29 using the title compound from Example 32.

EXAMPLE 34

5-O-Dimethoxytrityl-2-Thio-5-Methyl Uridine

2-Thio-5-methyl uridine (1 g, 3.6 mmol) was dissolved in dry pyridine and co-evaporated twice. The resulting yellow foam was dissolved in 25 mL of dry pyridine and dimethoxy-trityl chloride (1.8 g, 5.5 mmol) was added followed by 4,4-dimethylaminopyridine (0.050 g, 0.4 mmol). The reaction was allowed to stir overnight at room temperature. To the reaction mixture was added 1 mL of methanol. The solution was partitioned between 75 mL of saturated sodium bicarbonate and 50 mL of chloroform. The aqueous layer was extracted with two additional portions of chloroform and the organic layers combined and dried with magnesium sulfate. After removal of the drying agent via filtration the filtrate was concentrated to an orange oil and purified by silica gel column chromatography using methanol/chloroform gradient with 0.5% pyridine added to neutralize the silica gel.

EXAMPLE 35

5-O-Dimethoxytrityl-3'-t-butyldimethylsilyl-5-Methyl-2-thiouridine

5'-O-Dimethoxytrityl-2-thio-5-methyl uridine (1 g, 1.73 mmol) was co-evaporated twice with dry DMF and then dissolved in dry DMF and imidazole (0.141 g, 2.08 mmol) was added followed by (0.313 g, 2.08 mmol) of t-butyl-dimethylsilyl chloride. The reaction mixture was stirred overnight. The reaction was checked by TLC using ethyl acetate/hexane 1:1, which showed the reaction had gone to completion. The reaction mixture was then poured into 5% sodium bicarbonate and extracted 3 times with chloroform. The combined organic solution was dried with magnesium sulfate and concentrated to an oil. The resulting oil was purified by silica gel column chromatography using a methanol/chloroform gradient isolating separately the 2' and 3' silyl protected nucleoside.

EXAMPLE 36

5-O-Dimethoxytrityl-3'-t-Butyldimethylsilyl-2'-Methanesulfonyl-5-Methyl-2-Thiouridine 5'-O-Dimethoxytrityl-3'-t-butyldimethylsilyl-5-methyl-2-thiouridine (1.0 g, 1.45 mmoles) was dissolved in pyridine and cooled to 0° C. To this solution was added methanesulfonyl chloride (0.183 g, 1.6 mmoles) dropwise. The reaction was then allowed to stir until complete by TLC. The reaction mixture is neutralized with methanol and concentrated to an oil. The title compound is used as is for further reactions.

EXAMPLE 37

5'-DMT-3'-t-butyl dimethylsilyl-2,2' thio anhydro-5-methyl-2-thiouridine

The mesylated nucleoside found in Example 36 is treated at room temperature with 5 equivalents of sodium methoxide and allowed to stir until complete formation of the thioanhydro product. The solution is then neutralized with Dowex 50 W ($H^+$ form), the resin filtered off and the resulting solution concentrated to give the title compound.

EXAMPLE 38

2'-Fluoro-3'-t-butyl dimethylsilyl-5'-DMT-5-methyl-2-thiouridine

The thioanhydronucleoside found in Example 37 was dissolved in anhydrous dioxane. To this solution was added 6 equivalents of HF/Pyridine complex and the reaction stirred until complete by TLC. The reaction mixture is then poured over an equal volume of ice and calcium carbonate is added until neutral. The solids are filtered off and the filtrate is concentrated. The residue is purified by silica gel column chromatography to give the title compound.

EXAMPLE 39

2'-Fluoro-3'-O-[(N,N-diisopropylamino)-2-cyanoethoxyphosphite]-5'-DMT-5-methyl-2-thiouridine 2'-Fluoro-3'-t-butyl dimethylsilyl-5'-DMT-5-methyl-2-thiouridine is treated as per the procedure of Example 29 to give the title compound.

EXAMPLE 40

Assay for Oligonucleotide Inhibition of PKC-α mRNA Expression

A549 cells were plated in T-75 flasks (Falcon Labware, Lincoln Park, N.J.) and 24–48 h later (when 80–90% confluent) treated with 3 oligonucleotides of the following compositions.

| SEQ ID NO | Sequence |
|---|---|
| 1 | GTT CTC GCT GGT GAG TTT CA |
| 2 | GUU CUC GCT GGT GAG UUU CA |
| 3 | GUU CUC GCT GGT GAG UUU CA |

SEQ ID NO: 1 is a fully modified deoxyphosphorothioate, SEQ ID NO: 2 is a fully modified phosphorothioate that has 2'-fluoro at positions 1–6 and 15–20, and SEQ ID NO: 3 is a fully modified phosphorothioate that has 2'-fluoro-5-methyluridine at positions 2, 3, 5, and 16–18, and 2'-fluoros at positions 1, 4, 6, 15, 19, and 20.

Cells were washed twice with 10 ml of DMEM and 5 ml of DMEM containing 20 µg/ml DOTMA/DOPE solution (Lipofectin°) (Bethesda Research Laboratories) was added. The oligomeric compounds were then added to the required concentration from a 10 µM stock solution, and the solutions were mixed by swirling of the dish. The cells were incubated at 37° C. for 4 h, washed once with DMEM +10% FCS to remove the DOTMA/DOPE solution, and then an additional 20 ml of DMEM +10% FCS was added and the cells were allowed to recover for another 20 h.

A549 cells were treated with oligomeric compounds at 25, 50, 100, 200, and 400 nM concentrations, and total cellular RNA was isolated by lysis in 4M guanidinium isothiocyanate followed by a cesium chloride gradient. Total RNA (15–30 µg) was resolved on 1.2% agarose gels containing 1.1% formaldehyde and transferred to nylon membranes. The blots were then hybridized with bovine PKC-α cDNA obtained from the ATCC (Bethesda, Md.) (Coussens et al., 1986). The cDNA probes were $^{32}$P-radiolabeled with [α-$^{32}$P] dCTP by random primer labeling using a commercially available kit (Promega) according to the manufacturer's instructions. The filters were hybridized for 60 min in Quikhyb solution (Stratagene) at 68° C. This was followed by two low stringency washes (2×SSC/0.1% SDS) at room temperature and two high stringency washes (0.1×SSC/0.1% SDS) at 60° C. Hybridizing bands were visualized and quantitated using a PhosphorImager. The blots were then stripped of radioactivity by boiling and reprobed with a $^{32}$P-labeled glycerol-3-phosphate dehydrogenase probe (Clontech) to confirm equal RNA loading.

The 2'-Fluoro-5-methyl-uridine containing oligomeric compound SEQ ID NO: 3, showed a 10 fold increase in potency relative to SEQ ID NO: 1, the oligomeric compound having thymidines in the same positions. SEQ ID NO: 3 also showed a measurable increase in potency relative to SEQ ID NO: 2.

EXAMPLE 41

In vitro HIV Inhibition Assay

An in vitro transfection assay is used to identify oligonucleotides which inhibit the expression of the HIV rev protein. The time course of this assay is four days. The mouse embryonic fibroblast cell line (3T3) is maintained in a exponential growth phase in DMEM (High glucose) supplemented with 10% fetal calf serum, glutamine and antibiotics.

Plasmid construction: pHIV env-luc was constructed as follows. The 3.1 Kb SalI/XhoI fragment to pBH10 (20) which contains the Human immunodeficiency virus type 1 envelope gene (isolate BH10) (nucleotides 5150–8260), was ligated to the XhoI site of the pMAMBam plasmid to obtain pMAMHIVenv. pMAMBam vector was obtained by gel purification of a BamHI digest of the 8.3 Kb pMAMneo plasmid (Clontech). The BamHI site was destroyed by filling the ends with Klenow polymerase in the presence of all four dNTP's and subsequent ligation. pMAMHIV-env was cut at the unique BamHI site, the ends were filled with Klenow polymerase in the presence of all four dNTP's and religated. This procedure introduced a frameshift mutation which inactivates the Rev-coding part of the env gene. Finally, the SalI/SalI luciferase-encoding reporter gene was cloned upstream of the HIV sequence at the unique SalI site, to obtain the final construct pHIV env-luc harboring the mutated rev gene.

For the construction of the pSG5-rev plasmid, which expresses rev protein both in mammalian cells of in vitro with T7 RNA polymerase, an EcoRI/BglII rev cDNA was prepared by PCR from pCV1. The PCR fragment was cut with EcoRI and BglII and subcloned into the Eco/RI/BglII sites of the vector pSG5 (Stratagene). The PCR primers were:

5'-GCT CGG GAA TTC ATG GCA GGA AGA AGC GGA

5'-CTG GGA GAT CTC TAT TCT TTA GCT CCT GAC TC

Rep 6 prepared as per Miesfeld, R., et.al., *Cell*, 1986, 46, 389–399, a plasmid which expresses the full length glucocorticoid receptor under control of the constitutive RSV LTR.

Day 1: The 3T3 cells are washed and counted by trypan blue exclusion and seeded in each well of a 6-well microtiter plate at 8.5×10$^4$ cells per well.

Day 2: Three recombinant plasmids, pSG5, pHIV env-luc and Rep06 were precipitated using a standard CaPO$_4$ precipitation protocol (Graham, F. L. and van der Eb, A. J. *Virology*, 1973, 52, 456–467). The CaPO$_4$ precipitated DNA is added to the mouse embryonic fibroblasts and the cells are incubated for seven hours at 37° C. The cells are washed with phosphate buffered saline and incubated overnight at 37° C. in DMEM supplemented with 10% fetal calf serum, glutamine, antibiotics and a defined concentration of oligonucleotide and serial half log dilutions.

Day 3: The cells are washed twice with OPTimen media and then treated with 2.5mg/ml lipofectin per well in OPtimem media and oligonucleotide for four hours at 37° C. The lipofectin/oligonucleotide solution is replaced with complete media and the cells are allowed to recover at 37° C. for two hours. The oligonucleotide treated cells are then treated with Dexamethasone.

Day 4: 24 hours post Dexamethason treatment, the cells are lysed and a luciferase assay is carried out (Sigma Chemical Technical). The protein concentration of the lysed sample is determined using the Bradford protein assay (Bradford, M. *Anal. Biochem.*, 1976, 72, 248).

EXAMPLE 42

In Vivo Activity of Oligonucleotide 8469

Female Balb/c nude mice having s.c. transplanted human lung adenocarcinoma A549 are treated with oligonucleotide 8469-3, SEQ ID NO: 3, and vehicle (saline). The treatment is started as nine days and continued once daily for 33 days. Two dose regimens were studied one at 6.0 mg/kg i.v. and one at 0.6 mg/kg i.v.

Viable fragments (25–50 mg) of serially passed (3+times) s.c. tumors are reimplanted into study animals s.c. in one flank by trocar needle. When the fragments reach approximately 100 mg (5–15 days later),treatment begins. Animals are treated i.v., three to seven times per week until control tumors exceed 1 gram in size (ie, for 2–4 weeks). Tumor size is measured with calipers once or twice per week.

The results show a significant reduction in the tumor growth with the two dose regimens with the 6.0 mg/kg giving a slower rate of growth than the 0.6 mg/kg.

EXAMPLE 43

Effect of Oligomeric Compounds on PKC-α mRNA Levels

A549 cells are treated with oligomers SEQ ID NO: 1, SEQ ID NO: 2, and SEQ ID NO: 3 as described above, at doses from 100 to 400 Nm for four hours in the presence of the cationic lipids DOTMA/DOPE, washed and allowed to recover for an additional 20 hours. Total RNA is extracted and 20 µg of each is resolved on 1.2% gels and transferred to nylon membranes. These blots are probed with a $^{32}P$ radiolabeled PKC-α cDNA probe and then stripped and reprobed with a radiolabeled G3PDH probe to confirm equal RNA loading. PKC-α transcripts are examined and quantified with a PhosphorImager (Molecular Dynamics, Sunnyvale Calif.). A phosphorothioate oligonucleotide standard, known to be active against PKC-α, has an $IC_{50}$ in this assay of approximately 175 nM. Compounds exhibiting improved activity will have a greater activity than the test standard e.g. having a lower $ic_{50}$ than 175 nM. High specific binding of the test compounds to the PKC-α sequence can also be used to distinguish PKC-α mRNA from other mRNA of other PKC isozymes such as the beta, gama and delta isozymes.

EXAMPLE 44

Northern Blot Analysis of Ras Expression in vivo

Cells are treated with oligomers SEQ ID NO: 1, SEQ ID NO: 2, and SEQ ID NO: 3 as described above in Opti-MEM reduced-serum medium containing 2.5 µL DOTMA. Oligomers are then added to the desired concentration. After 4 hours of treatment, the medium is replaced with medium without oligonucleotide. Cells are harvested 48 hours after oligomer treatment and RNA is isolated using a standard CsCl purification method. Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, N.Y.

The RNA is analyzed by northern hybridization analysis using 10 µg of each RNA. The RNA is electrophoresed on a 1.2% agarose/formaldehyde gel and transferred overnight to GeneBind 45 nylon membrane (Pharmacia LKB, Piscataway, N.J.) using standard methods. Kingston, R. E., in Current *Protocols in Molecular Biology*, (F. M. Ausubel, R. Brent, R. E. Kingston, D. D. Moore, J. A. Smith, J. G. Seidman and K. Strahl, eds.), John Wiley and Sons, N.Y. RNA was UV-crosslinked to the membrane. Double-stranded $^{32}P$-labeled probes are synthesized using the Prime a Gene labeling kit (Promega, Madison Wis.). The ras probe is a SaiI-NheI fragment of a cDNA clone of the activated (mutant) H-ras mRNA having a GGC-to-GTC mutation at codon-12. The control probe is G3PDH. Blots were prehybridized for 15 minutes at 68° C. with the QuickHyb hybridization solution (Stratagene, La Jolla, Calif.). The heat-denatured radioactive probe (2.5×106 counts/2 ml hybridization solution) mixed with 100 µL of 10 mg/ml salmon sperm DNA was added and the membrane was hybridized for 1 hour at 68° C. The blots were washed twice for 15 minutes at room temperature in 2×SSC/0.1% SDS and once for 30 minutes at 60° C. with 0.1×SSC/0.1% SDS. Blots were autoradiographed and the intensity of signal was quantitated using an ImageQuant PhosphorImager (Molecular Dynamics, Sunnyvale, Calif.). Northern blots are first hybridized with the ras probe, then stripped by boiling for 15 minutes in 0.1×SSC/0.1% SDS and rehybridized with the control G3PDH probe to check for correct sample loading.

What is claimed is:

1. An oligomeric compound comprising at least one monomeric sub-unit of structure I:

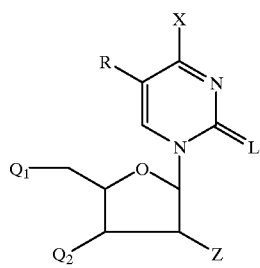

Structure I wherein:

X is amino;

R is methyl;

L is oxygen;

Z is —O—$CH_3$; and one of $Q_1$ and $Q_2$ is attached via a phosphorothioate linking moiety to a nucleotide, oligonucleotide, nucleoside, or oligonucleoside and the other of said $Q_1$ and $Q_2$, is a hydroxyl, a protected hydroxyl, an activated solid support, a nucleotide, an oligonucleotide, a nucleoside, an oligonucleoside, an oligo-nucleotide/nucleoside, an activated phosphate, a phosphate, an activated phosphite, or a phosphite;

provided that said linking moiety is not a sulfamate group.

2. An oligomeric compound comprising at least one monomeric sub-unit of structure I:

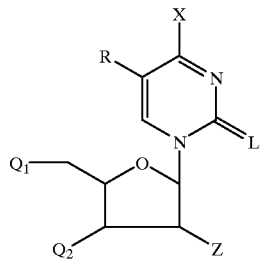

Structure I wherein:

X is amino;

R is methyl;

L is oxygen;

Z is O—$R_1X_1$, where $R_1$ is $C_1$–$C_6$ alkyl, and $X_1$ is H; and one of $Q_1$ and $Q_2$ is attached via a phosphorothioate linking moiety to a nucleotide, oligonucleotide, nucleoside, or oligonucleoside and the other of said $Q_1$ and $Q_2$, is a hydroxyl, a protected hydroxyl, an activated solid support, a nucleotide, an oligonucleotide, a nucleoside, an oligonucleoside, an oligo-nucleotide/nucleoside, an activated phosphate, a phosphate, an activated phosphite, or a phosphite;

provided that said linking moiety is not a sulfamate group.

3. An oligomeric compound comprising at least one monomeric sub-unit of structure I:

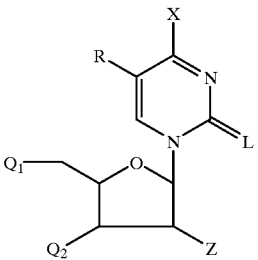

Structure I wherein:

X is amino;

R is methyl;

L is oxygen;

Z is O—$R_1X_1$, where $R_1$ is substituted $C_1$–$C_6$ alkyl, and $X_1$ is H; and one of $Q_1$ and $Q_2$ is attached via a phosphorothioate linking moiety to a nucleotide, oligonucleotide, nucleoside, or oligonucleoside and the other of said $Q_1$ and $Q_2$, is a hydroxyl, a protected hydroxyl, an activated solid support, a nucleotide, an oligonucleotide, a nucleoside, an oligonucleoside, an oligonucleotide/nucleoside, an activated phosphate, a phosphate, an activated phosphite, or a phosphite;

provided that said linking moiety is not a sulfamate group.

* * * * *

```
                         SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: Nucleic Acid Analog (xi) SEQUENCE DESCRIPTION: SEQ ID NO:1:

GTT CTC GCT GGT GAG TTT CA                                              20

(2) INFORMATION FOR SEQ ID NO:2:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: Nucleic Acid Analog (xi) SEQUENCE DESCRIPTION: SEQ ID NO:2:

GUU CUC GCU GGU GAG UUU CA                                              20

(2) INFORMATION FOR SEQ ID NO:3:

(i) SEQUENCE CHARACTERISTICS:
```

```
            (A) LENGTH: 20 base pairs
            (B) TYPE: nucleic acid
            (C) STRANDEDNESS: single
            (D) TOPOLOGY: linear (ii) MOLECULE TYPE: Nucleic Acid Analog (xi) SEQUENCE DESCRIPTION: SEQ ID NO:3:

GUU CUC GCT GGT GAG UUU CA                                          20
```